(12) United States Patent
Lin

(10) Patent No.: US 10,010,713 B2
(45) Date of Patent: Jul. 3, 2018

(54) NERVE STIMULATION DEVICE FOR TREATING OR REDUCING PARALYSIS

(71) Applicant: The Regents of the University of California, Oakland, CA (US)

(72) Inventor: Harrison W. Lin, Encinitas, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/094,594

(22) Filed: Apr. 8, 2016

(65) Prior Publication Data

US 2016/0296753 A1    Oct. 13, 2016

Related U.S. Application Data

(60) Provisional application No. 62/145,348, filed on Apr. 9, 2015.

(51) Int. Cl.
*A61N 1/36* (2006.01)
*A61N 1/05* (2006.01)

(52) U.S. Cl.
CPC ....... *A61N 1/36003* (2013.01); *A61N 1/0526* (2013.01); *A61N 1/0551* (2013.01)

(58) Field of Classification Search
CPC . A61N 1/36003; A61N 1/0526; A61N 1/0551
See application file for complete search history.

(56) References Cited

U.S. PATENT DOCUMENTS

2010/0114240 A1* 5/2010 Guntinas-Lichius ... A61N 1/36003
                                                                    607/48
2013/0304174 A1    11/2013 Langhals et al.

OTHER PUBLICATIONS

Brudny et al., Electromyographic rehabilitation of facial function and introduction of a facial paralysis grading scale for hypoglossal-facial nerve anastomosis. Laryngoscope, Apr. 1988; 98:405-10.
(Continued)

*Primary Examiner* — Paula J Stice
(74) *Attorney, Agent, or Firm* — Shimokaji IP

(57) ABSTRACT

Disclosed herein is a method of treating a disease, comprising: (a) implanting an array of electrodes on one or more targeted nerves and/or targeted muscles; and (b) treating the disease by selectively stimulating the one or more targeted nerves and/or targeted muscles through electrical pulses delivered from the array. Also disclosed herein is a device, comprising a plurality of electrodes that have the capacity to be inserted in a facial nerve. Further disclosed herein is a method of treating facial paralysis and/or damage in a subject, comprising: (a) detecting the level of contraction of individual muscles on a healthy, non-paralyzed side of the face of the subject; and (b) treating facial paralysis by a direct targeted stimulation of the corresponding muscles or nerve fibers on a paralyzed side of the face of the subject. Also disclosed herein is a method of treating synkinesis, comprising: (a) implanting an array of electrodes on one or more targeted nerves and/or targeted muscles; and (b) selectively suppressing the one or more targeted nerves and/or targeted muscles through electrical pulses delivered from the array.

11 Claims, 10 Drawing Sheets

(56) References Cited

OTHER PUBLICATIONS

Ruboyianes et al. The maximal stimulation and facial nerve conduction latency tests: Predicting the outcome of bell's palsy. Laryngoscope, Jan. 1994; 104:1-6.
Yatsenko et al., Simultaneous, proportional, multi-axis prosthesis control using multichannel surface EMG. IEEE Engineering in Medicine and Biology Society Annual Conference, Aug. 2007: 6134-6137.
McDonnall et al., Verification and validation of an electrode array for a blink prosthesis for facial paralysis patients; Neural Engineering (NER), 2013 6th International IEEE/EMBS Conference. Nov. 2013. pp. 1167-1170.
Langhals et al., Update in facial nerve paralysis: tissue engineering and new technologies. Current Opinions in Otolaryngology Head and Neck Surgery, Aug. 2014; 22:291-9.

\* cited by examiner

NERVE STIMULATION DEVICE FOR TREATING OR REDUCING PARALYSIS

CROSS-REFERENCE TO RELATED APPLICATIONS

The present application claims the benefit of priority under 35 U.S.C. § 119(e) of provisional application Ser. No. 62/145,348, filed Apr. 9, 2015, the contents of which are hereby incorporated by reference.

FIELD OF INVENTION

The present disclosure is in the medical and biomedical field, and more specifically in the field of treating or reducing paralysis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Permanent facial paralysis is a difficult challenge for patients and physicians, as it creates both substantial functional and psychological problems for the patient. Unfortunately, facial paralysis is not an uncommon problem: the annual incidence has been estimated to be approximately 70 cases per 100,000. An estimated 127,000 new cases of permanent facial paralysis are diagnosed annually in the United States alone.

Current treatment involves free tissue microvascular transfer of an isolated muscle to the face and connecting its nerve to a motor nerve in the head and neck area (e.g. masseter or hypoglossal nerve, or nerve graft originating from the contralateral and functional facial nerve). This surgery, along with other dynamic facial reanimation surgeries, is currently performed in a small number of tertiary care centers around the world. The surgeries are lengthy and at times multi-staged, involve at least two vascular and one neural microanastamoses, only provide some semblance of a smile, and do not address the eye. Accordingly, these procedures (1) may not be optimal or offered to patients with substantial co-morbidities who may not tolerate one or more 6 to 12 hour surgeries under general anesthesia, (2) require head and neck surgeons with highly-specialized training and expert familiarity with surgical anatomy outside the head and neck, and (3) typically only provide patients with, on average, eight millimeters (~⅓ of an inch) of oral commissure excursion in a non-spontaneous fashion (Hadlock et al., 2011). Patients and families often have to travel hundreds if not thousands of miles to be treated at one of very few facial nerve centers in the United States and internationally. These personal expenditures, along with the tremendous health care costs of the surgeries, several days of intensive care unit admission for free tissue graft monitoring, and work intensive postoperative care and physical therapy, can be quite substantial. Moreover, because the nerve in the head and neck has to slowly grow into the nerve and muscle of the free graft, results are not immediate and take ~6 to 18 months to emerge. Finally, in about 10% of the patients, the free gracilis muscle does not survive. These patients need to return to operating room under general anesthesia to remove the necrotic muscle graft and be left as they were before the initial surgery, only now with a large facial scar.

Another currently available option involves introducing non-muscular material to the face with the goal of improving facial symmetry and oral or blink function. For example, connective tissue from the thigh can be harvested and transferred to the face to pull the corner of the mouth superiorly or to dilate a collapsed nasal valve. Moreover, an inert metal weight can be inserted into the upper eyelid to passively assist in eye closure. These interventions are intended only to moderately improve function and provide no dynamic movement to the paralyzed side of the face. In summary, the results of these invasive surgeries, when compared to the resting and dynamic states of the face prior to the onset of facial paralysis, are frequently suboptimal.

Thus there is a need in the art for novel and more effective treatments for muscle and nerve damage, including facial paralysis.

SUMMARY OF THE INVENTION

In various embodiments, disclosed herein is a method of treating a disease, comprising: (a) implanting an array of electrodes on one or more targeted nerves and/or targeted muscles; and (b) treating the disease by selectively stimulating the one or more targeted nerves and/or targeted muscles through electrical pulses delivered from the array. In some embodiments, the disease is associated with nerve damage or muscle damage. In some embodiments, the disease is paralysis. In some embodiments, the disease is facial paralysis. In some embodiments, the array of electrodes are positioned in one or more firm shanks. In some embodiments, the selective stimulation of one or more targeted nerves comprises independently exciting specific nerve fiber populations that generate isolated movements in the said nerve fiber populations. In some embodiments, the method of treating the disease further comprise mapping of muscle movements of healthy targeted nerves and/or targeted muscles. In one of these embodiments, the mapping of muscle movements comprises detecting the presence and extent of contractions of individual healthy muscles. In one embodiment, the contractions of individual healthy muscles are detected by sensors adhered to the skin. In another embodiment, the method further comprises transmitting muscle movements to an implanted device. In another embodiment, the method further comprises transmitting a correspondingly graded stimulation of the same muscle on the paralyzed side.

In various embodiments, disclosed herein is a device, comprising a plurality of electrode sites that have the capacity to be inserted in a facial nerve. In some embodiments, the device further comprises a receiver stimulator. In some embodiments, the device further comprises a grounding electrode. In some embodiments, the plurality of electrode sites are positioned in one or more firm shanks. In some embodiments, the device has the capacity to receive electromyogenic information from the opposite side of the face. In some embodiments, the electromyogenic information is transmitted wirelessly by an epidermal electronic device. In some embodiments, one or more electrodes stimulate a set of neural fibers within the facial nerve responsible for specific movements of the face. In one embodiment, the device is useful for treating or reducing facial paralysis, wherein the device comprises: (a) implanting the device on the paralyzed side of the face, and wherein the plurality of electrode sites is inserted into the mastoid segment of the facial nerve; (b) placing an epidermal electronic device on the healthy, non-paralyzed side of the face, wherein the epidermal electronic device communicates wirelessly with the device when it detects contractions of the facial muscles; and (c) providing a programmed and graded stimulus to the appropriate electrode, and thereby generating a symmetric contraction of the corresponding muscle on the paralyzed side. In one embodiment, the device aids in achieving dynamic and spontaneous facial symmetry in a patient afflicted with facial paralysis.

In various embodiments, disclosed herein is a method of treating facial paralysis and/or damage in a subject, comprising: (a) detecting the level of contraction of individual muscles on a healthy, non-paralyzed side of the face of the subject; and (b) treating facial paralysis by a direct targeted stimulation of the corresponding muscles or nerve fibers on a paralyzed side of the face of the subject. In some embodiments, the direct targeted stimulation of facial nerve fibers are responsible for isolated movements of the face. In some embodiments, the targeted stimulation of facial nerve fibers is achieved by implanting, in a facial nerve, a device comprising a plurality of electrode sites. In some embodiments, the detection of the level of contraction of individual muscles on the healthy, non-paralyzed side of the face is achieved through an epidermal electronic device that detects contractions of facial muscles. In some embodiments, the epidermal electronic device communicates the contractions with a second device implanted on the paralyzed side of the face.

In various embodiments, disclosed herein is a method of treating synkinesis, comprising: (a) implanting an array of electrodes on one or more targeted nerves and/or targeted muscles; and (b) treating synkinesis by selectively suppressing the one or more targeted nerves and/or targeted muscles through electrical pulses delivered from the array. In some embodiments, the selective suppression of one or more targeted nerves comprises independently suppressing specific nerve fiber populations that generate isolated movements in the said nerve fiber populations. In some embodiments, the array electrodes comprise a sixteen channel electrode array. In some embodiments, the method further comprises mapping of muscle movements of healthy targeted nerves. In some of these embodiments, the mapping of muscle movements comprise detecting the presence and/or extent of contractions of individual healthy muscles. In some embodiments, the contractions of individual healthy muscles are detected by sensors adhered to the skin. In some embodiments, the selective suppression of nerve fibers is achieved by penetrating the array of the one of more electrode sites into the main trunk of the facial nerve, and delivering suppressive electrical current pulses to each nerve that is to be suppressed.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
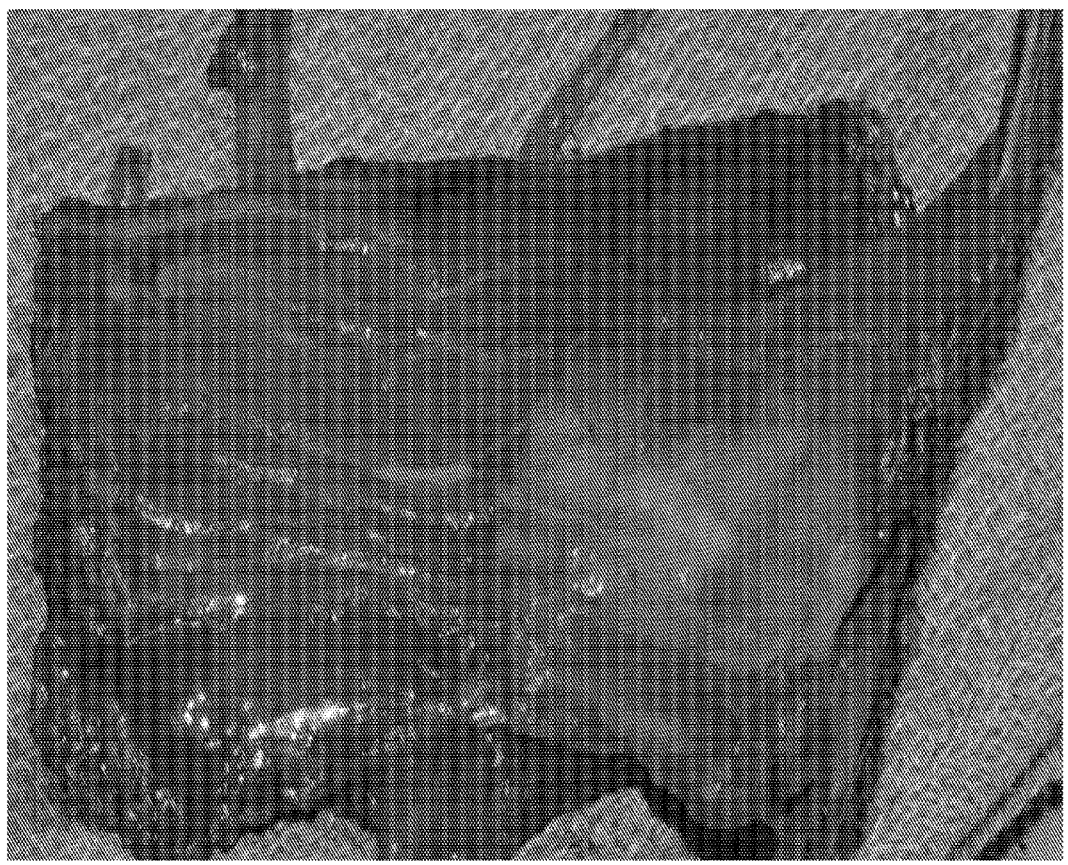
FIG. 1 depicts the gracilis muscle, along with its principle nerve, artery and vein, is harvested from the thigh through a lengthy incision in the groin area.

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As described herein, currently patients with permanent unilateral facial paralysis have very few effective options to restore dynamic and volitional (spontaneous and emotionally-driven) function to the weak side of their face. Surgeries to solely provide a minimal upward movement of the corner of the mouth involve transplanting a bulky thigh muscle into the face in one or more 6 to 12 hour invasive surgeries under general anesthesia followed by a three to five day hospital stay, if there are no major complications. In accordance with various embodiments herein, the present invention in one example includes placing a stimulating array with one or more electrode sites into the facial nerve to independently excite specific nerve fiber populations that generate isolated movements of the face (say, for example, brow raise, blink, or smile). In one embodiment, the present invention provides a device that can be installed in a safe, routine, two-hour outpatient surgery that only requires a small incision (say, for example, about 2-inch) hidden behind the ear. In accordance with various embodiments herein, the present invention provides a method of treatment that includes a surgery that can be performed, for example, by any general otolaryngologist and would not require any post-residency fellowship training. Soon after the surgery, in another embodiment, facial movements elicited by each individual electrode can be mapped. For example, in one embodiment, electrode #1 could be found to stimulate raising of the eyebrow, while electrode #3 causes the eyelid to blink, and electrode #8 generates a robust smile. Furthermore, in another embodiment, sensors that detect contraction of muscle in the non-paralyzed (normal) side of the face, either placed and camouflaged on the skin or implanted into the muscle, would detect both the contraction and the extent of the contraction (e.g. minimal, moderate or maximal effort), wirelessly transmit this information to the implanted device, and trigger a correspondingly graded stimulation of the same muscle on the paralyzed side of the face. This would generate complete or near-complete dynamic and spontaneous facial symmetry of the entire face. As readily apparent to one of skill in the art, this result is far more advantageous and effective than the alternatives for patients today, including transplant of a large thigh muscle to the delicate face with a lengthy and visible facial incision only to generate less than one centimeter of movement at the mouth in a non-spontaneous, non-emotional fashion (i.e. patients need to remember to move the muscle when they smile). In accordance with various embodiments herein, the present invention provides a method of improving patient facial function and cosmetic outcomes, and/or reducing surgical time, hospital stays, and associated costs and risks.

In one embodiment, the present invention provides a method of treating facial paralysis and/or damage comprising selective stimulation of facial nerve fibers responsible for isolated movements of the face, and/or detection of the level of contraction of individual muscles on the normal (non-paralyzed) side of the face to direct targeted stimulation of the corresponding muscles on the paralyzed side of the face.

In another embodiment, the present invention provides a device that provides detection of the level of contraction of individual muscles on the normal (non-paralyzed) side of the face to direct targeted stimulation of the corresponding muscles on the paralyzed side of the face. In another embodiment, the device is an implantable device. In another embodiment, the device is modified cochlear implant technology that can receive wireless electromagnetic signals to provide programmable and graded electric current to one or more of its stimulating electrodes on its array. In another embodiment, the attached array on the device is a firm, sharpened shank to penetrate and reside within the facial nerve. In another embodiment, the modified device is described in FIG. 3 herein. In another embodiment, wireless signals convey electromyogenic information from the normal side of the face.

In another embodiment, the present invention provides a device comprising one or more of the following: (1) receiver-stimulator, (2) grounding electrode, and/or (3) multi-channel penetrating electrode array. In another embodiment, the penetrating array would be surgically inserted into the mastoid segment of an injured and poorly-functioning facial nerve. Intraoperative electromyographic testing could confirm that all functionally and cosmetically critical muscles and actions of the face, including blink and smile movements, can be adequately stimulated by the device and its placement within the nerve. Postoperatively, for example, stimulation thresholds for individual facial muscles could be evaluated for each of the electrodes. There are then, for example, several ways in which such an electrode array could be used for prosthetic muscle stimulation at rest and during facial motion. To begin, constant low-level electrical stimulation could be programmed to provide tone; this would provide a baseline level of contraction to the muscles, contribute to muscular bulk, and provide facial symmetry at rest and improved oral competence. Furthermore, a programmed and regularly-intervaled stimulation of the orbicularis oculi would create consistent blink function and improve the ocular/corneal condition.

In another embodiment, the present invention provides a system that includes implantable and/or transcutaneous electromyographic recording devices that would detect contraction of critical muscles on the contralateral (normal) side of the face. In one embodiment, sensors could be implanted on the skin or into the muscles of the functional side of unilateral facial paralysis patients to detect contractions of the face. In another embodiment, the sensors would then communicate in real-time with the implant on the ipsilateral (paralyzed) size, and the implant device would then stimulate a graded/proportional symmetric contraction of the very same facial muscles. In one embodiment, the communication is done wirelessly.

In one embodiment, the present invention relates to the ability of an intraneural multichannel electrode array to selectively stimulate neural populations that innervate distinct facial muscles. In one embodiment, the concepts and technique used to stimulate the neural populations are analogous to the technique described herein for using the penetrating array in the auditory nerve, with stimulation sites in intimate contact with nerve fibers. In one embodiment, studies in short-term animal experiments showed that this intraneural stimulation, compared to the conventional intrascalar CI electrode array, offered more precise excitation of frequency-specific nerve populations, access to the entire frequency range of hearing, greatly reduced interference among channels, substantially lower thresholds, and improved transmission of temporal fine structure. In one embodiment, these observations form a basis for clinical use of intra-neural stimulation in other cranial nerves, such as, for example, the facial nerve. In one embodiment, the selectivity of stimulation in a facial muscle through individual electrode discharges may be improved or refined by refining the electrode material and surface area, and current characteristics, among other variables. In one embodiment, the present invention stimulates restricted neural populations of the facial nerve in an effort to elicit contractions of specific facial muscles.

In one embodiment, the inventors have demonstrated the successful use of bioelectric neuro-prosthetic technologies to the facial nerve. Bioelectric and direct nerve-electrode interface technologies are now routinely available in clinical practice. Vagal nerve and deep brain stimulators are frequently implanted into patients to effectively treat a variety of common neurologic and psychiatric pathologies. Chronic spinal cord stimulators are likewise in routine use for patients with severe neuropathic pain recalcitrant to conservative, non-invasive therapy. A surgically-implanted device to electrically stimulate the hypoglossal nerve in patients with severe obstructive sleep apnea has been shown in clinical trials to effectively improve subjective and objective measures of sleep apnea. Lower extremity nerves have also been the target of direct electrical stimulation to improve bladder, bowel and sexual function in both animal and human trials. Finally, the cochlear implant (CI) brings useful hearing and speech recognition to profoundly deaf people. In one embodiment, the inventors have demonstrated the use of bioelectric technologies, such as the above, to the facial nerve.

In one embodiment, selectivity of the desired muscle stimulation may be improved by a change or modification in the materials, design, and dimensions of electrodes and arrays. In one embodiment, highly-selective stimulation of neural fibers innervating only the palpebral portion of the orbicularis oculi may provide patients with a natural-appearing gentle blink, and tremendous functional and cosmetic benefit. In one embodiment, the intra-neural electrode array may be chronically-implanted into the facial nerve. This helps in steadily maintaining function over a period of months to years and provides the face with muscular tone.

In one embodiment, disclosed herein is a cochlear implant-like programmable device with one (or more) multi-channel penetrating electrode array that can be surgically and securely inserted into the mastoid segment of an injured and poorly-functioning facial nerve. In one embodiment, intraoperative electromyographic testing confirms that all functionally and cosmetically critical muscles of the face are adequately stimulated by the array.

In one embodiment, graded stimulation levels for individual facial muscles are evaluated post-operatively. In one embodiment, the detection of patient-initiated electrical neural or myogenic signals that subsequently deliver messages to and activate a secondary device is of considerable interest in military research laboratories to address the needs of veteran amputees and improve the functionality of prosthetic limbs. In one embodiment, disclosed herein is a wired or wireless system, which provides for transcutaneous or intra-muscular detection of individual muscle contraction on the contralateral (normal/functional) side and consequent, simultaneous, and effort-matched stimulation of the same muscles on the paralyzed side.

In various embodiments, disclosed herein is a method of treating a disease, comprising: (a) implanting an array of one or more electrode sites on one or more targeted nerves and/or one or more targeted muscles; and (b) selectively stimulating the one or more targeted nerves and/or one or more targeted muscles through electrical pulses delivered from the array of one or more electrode sites. In some embodiments, the disease is associated with nerve damage or muscle damage. In some embodiments, the disease associated with nerve damage or muscle damage is paralysis. In some embodiments, the disease associated with nerve damage or muscle damage is facial paralysis. In some embodiments, the selective stimulation of one or more targeted nerves comprises independently exciting specific nerve fiber populations that generate isolated movements in the said nerve fiber populations. In some embodiments, the method of treating the disease further comprise mapping of muscle movements of healthy targeted nerves and/or targeted muscles. In one of these embodiments, the mapping of muscle movements comprises detecting the presence and extent of contractions of individual healthy muscles. In one embodiment, the contractions of individual healthy muscles are detected by sensors adhered to the skin. In one embodiment, the contractions of the individual healthy muscles are detected and transmitted to an implanted device. In some of these embodiments, the device transmits a correspondingly graded stimulation of the same muscle on the paralyzed side.

In some embodiments, the array of one of more electrode sites are positioned in one or more firm shanks. In one embodiment, the implanted device may comprise a shank with multiple prongs. In another embodiment the implanted device comprises multiple shanks, wherein each of those shanks comprises one or more electrode sites. In one embodiment, the multi-prong or multi-shank implant may diversify the neural populations that come into contact with the electrodes. In one embodiment, the firm shank comprises a sixteen channel electrode array. In another embodiment, the firm shank comprises an electrode array of more than 16 electrode channels. In another embodiment, the firm shank comprises an electrode array of less than 16 electrode channels In various embodiments, disclosed herein is a device, comprising a plurality of electrode sites that have the capacity to be inserted in a facial nerve. In some embodiments, the device further comprises a receiver stimulator. In some embodiments, the device further comprises a grounding electrode. In some embodiments, the plurality of electrode sites is placed in a firm shank. In some embodiments, the device has the capacity to receive electromyogenic information from the opposite side of the face. In some embodiments, the electromyogenic information is transmitted wirelessly by an epidermal electronic device. In some embodiments, one or more electrodes in the device stimulate a set of neural fibers within the facial nerve responsible for specific movements of the face. In one embodiment, the device is useful for treating facial paralysis, and comprises (a) implanting the device on the paralyzed side of the face, and wherein the penetrating multi-channel electrode array is inserted into the mastoid segment of the facial nerve; (b) placing an epidermal electronic device on the healthy, non-paralyzed side of the face, wherein the epidermal electronic device communicates wirelessly with the firm shank device when it detects contractions of the facial muscles; and (c) providing a programmed and graded stimulus to the appropriate electrode and generating a symmetric contraction of the corresponding muscle on the paralyzed side. In one embodiment, the device aids in achieving dynamic and spontaneous facial symmetry in a patient afflicted with facial paralysis. The terms "epidermal electronics" or "epidermal electronic device," as used herein, contemplates a small, flexible device that attach to the skin and has the ability to monitor physiological signals. In one embodiment, epidermal electronics are devices as described by Kim et al (Dae-Hyeong Kim et al, Science, 12 Aug. 2011: Vol. 333, Issue 6044, pp. 838-843).

In various embodiments, disclosed herein is a method of treating facial paralysis and/or damage, comprising: (a) detection of the level of contraction of individual muscles on the normal (non-paralyzed) side of the face; and (b) treating facial paralysis by direct targeted stimulation of the corresponding muscles or nerve fibers on the paralyzed side of the face. In some embodiments, the targeted stimulation of facial nerve fibers is responsible for isolated movements of the face. In some embodiments, the selective stimulation of facial nerve fibers is achieved by implanting, in a facial nerve, a device comprising a plurality of electrode sites. In some embodiments, the detection of the level of contraction of individual muscles on the non-paralyzed side of the face is achieved through an epidermal electronic device that detects contractions of facial muscles. In some of these embodiments, the epidermal electronic device communicates the contractions wirelessly to a second device implanted on the paralyzed side of the face.

In various embodiments, disclosed herein is a method of treating synkinesis, comprising: (a) implanting an array of one or more electrode sites on one or more targeted nerves and/or one or more targeted muscles; and (b) selectively suppressing the one or more targeted nerves and/or one or more targeted muscles through electrical pulses delivered from the array of one or more electrode sites. In some embodiments, the selective suppression of one or more targeted nerves comprises independently exciting specific nerve fiber populations that generate isolated movements in the said nerve fiber populations. In some embodiments, the method of treating synkinesis further comprises mapping of muscle movements of healthy targeted nerves. In some of these embodiments, the mapping of muscle movements comprises detecting the presence and/or extent of contractions of individual healthy muscles. In some embodiments, the contractions of individual healthy muscles are detected by sensors adhered to the skin. In some embodiments, the selective suppression of nerve fibers is achieved by penetrating the array of the one of more electrode sites into the main trunk of the facial nerve, and delivering suppressive electrical current pulses to each nerve that is to be suppressed. In one embodiment, the array of one of more electrode sites comprises a sixteen channel electrode array.

In another embodiment, a second device may be implanted on the non-paralyzed side of the patient's face. In one embodiment, this second device may be implanted behind the ear. In some embodiments, the second device is receiver-transmitter comprising (i) a small transmitter, and (ii) one or more EMG-detecting wired arrays originating from the transmitter, wherein the working/distal end of each array may be surgically placed into one or more key facial muscles of the non-paralyzed side. In some embodiments, the one or more EMG-detecting wired arrays comprise 3 to 6 wired arrays which are surgically implanted into 3 to 6 key facial muscles. In some embodiments, the detected EMG signals would be picked up, delivered via the wire to the transmitter, and then transmitted wirelessly to the implanted device on paralyzed side, where graded, symmetric stimulation of the corresponding muscle(s) would be enacted. In one embodiment, implanting the second device may be more convenient for the patient.

The present invention is also directed to a kit to treat facial paralysis and nerve damage. The kit is an assemblage of materials or components, including at least one of the inventive compositions. Thus, in some embodiments the kit contains a composition including surgical tools and solution to implant sensors and electrodes for the treatment and monitoring of facial paralysis, as described above.

The exact nature of the components configured in the inventive kit depends on its intended purpose. For example, some embodiments are configured for the purpose of treating nerve damage. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as the detection of the level of contraction of individual muscles. Or, for example, surgical tools and materials that may be used when implanting one or more devices as described herein. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overview

Currently patients with permanent unilateral facial paralysis have very few effective options to restore dynamic and volitional (spontaneous and emotionally-driven) function to the weak or paralyzed side of their face. Surgeries to solely provide a minimal upward movement of the corner of the mouth involve transplanting a bulky thigh muscle into the face in one or more 6 to 12 hour invasive surgeries under general anesthesia followed by a three to five day hospital stay, if there are no major complications. In one embodiment, the invention involves placing a stimulating array with multiple electrode sites into the facial nerve to independently excite specific nerve fiber populations that generate isolated movements of the face (e.g. brow raise, blink, or smile). The device can be installed in a safe, routine, two-hour outpatient surgery that only requires a small 2-inch incision completely hidden behind the ear. In one embodiment, this surgery could be performed by any general otolaryngologist and would not require any post-residency fellowship training. Soon after the surgery, facial movements elicited by each individual electrode can be mapped; for example, electrode #1 could be found to stimulate raising of the eyebrow, while electrode #3 causes the eyelid to blink, and electrode #8 generates a robust smile. Furthermore, sensors that detect contraction of muscle in the non-paralyzed (normal) side of the face, either placed and camouflaged on the skin or implanted into the muscle, would detect both the contraction and the extent of the contraction (e.g. minimal, moderate or maximal effort), wirelessly transmit this information to the implanted device, and trigger a correspondingly graded stimulation of the same muscle on the paralyzed side of the face. This would generate complete or near-complete dynamic and spontaneous facial symmetry of the entire face. This can be contrasted with the current best option for patients today: transplant of a large thigh muscle to the delicate face with a lengthy and visible facial incision only to generate less than one centimeter of movement at the mouth in a non-spontaneous, non-emotional fashion (i.e. patients need to remember to move the muscle when they smile). In one embodiment, the present invention has the ability to (1) dramatically improve patient facial function and cosmetic outcomes, and (2) substantially reduce surgical time, hospital stays, and their associated costs and risks.

Example 2

Development

Figure 3:
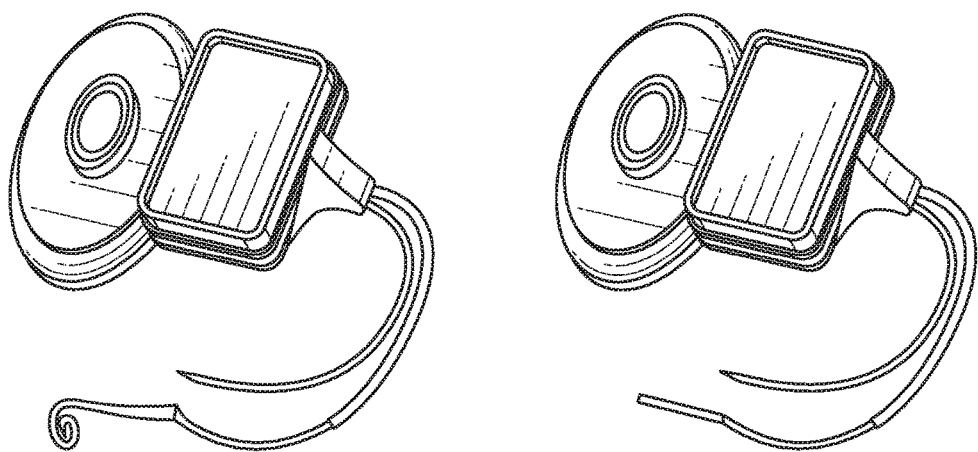
FIG. 3 depicts, in accordance with embodiments herein, a standard cochlear device and a device for treating facial paralysis.

In one embodiment, the present invention provides (1) selective stimulation of facial nerve fibers responsible for isolated movements of the face, and (2) detection of the level of contraction of individual muscles on the normal (non-paralyzed) side of the face to direct targeted stimulation of the corresponding muscles on the paralyzed side of the face. This implantable device would receive wireless electromagnetic signals to provide programmable and graded electric current to one or more of its stimulating electrodes on its array. The attached array on the device could be a firm, sharpened shank to penetrate and reside within the facial nerve (FIG. 3). In the cochlear implant, the wireless signals originate from an external processor receiving sound information. On the other hand, in the instant facial nerve implant, the signals would convey electromyogenic information from the normal (non-paralyzed) side of the face.

Previous research has demonstrated the utility of a penetrating multi-channel electrode array to selectively stimulate specific neural fibers within the cochlear nerve. By placing the electrode in direct contact with neural tissue (rather than into the fluid-filled cochlea distant from the cochlear nerve), the inventor, in one embodiment, found that intraneural stimulation provides far superior sound information to the higher level auditory centers in the brainstem. Furthermore, the inventor demonstrated the ability of this same electrode, when inserted into the facial nerve, to stimulate movement in specific regions of the face of a Guinea pig.

In one embodiment, the implantable device includes (1) receiver-stimulator, (2) grounding electrode, and (3) multichannel penetrating electrode array. The penetrating array would be surgically inserted into the mastoid segment of an injured and poorly-functioning facial nerve. Intraoperative electromyographic testing could confirm that all functionally and cosmetically critical muscles and actions of the face, including blink and smile movements, can be adequately stimulated by the device and its placement within the nerve. Postoperatively, stimulation thresholds for individual facial muscles could be evaluated for each of the electrodes. There are then several ways in which such an electrode array could be used for prosthetic muscle stimulation at rest and during facial motion. To begin, constant low-level electrical stimulation could be programmed to provide tone; this would provide a baseline level of contraction to the muscles, contribute to muscular bulk, and provide facial symmetry at rest and improved oral competence. Furthermore, a programmed and regularly-intervaled stimulation of the orbicularis oculi would create consistent blink function and improve the ocular/corneal condition.

In another embodiment, the system includes implantable or transcutaneous electromyographic recording devices would detect contraction of critical muscles on the contralateral (normal) side of the face. Recording and transmitting devices for physiologic measurements have in recent years become exceedingly miniaturized; for instance, Kim et al. described transcutaneous recording and transmitting "tattoos" or epidermal electronic devices (FIG. 4) that can accurately perform electrocardiography, electroencephalography, and electromyography, all without any wires. Such sensors may be implanted on the skin or into the muscles of the functional side of unilateral facial paralysis patients to detect contractions of the face. The sensors would then wirelessly communicate in real-time with the implant on the ipsilateral (paralyzed) size, and the implant device would then stimulate a graded/proportional symmetric contraction of the very same facial muscles.

Example 3

Benefits (1) Less expensive. Currently, the main option for patients with unilateral permanent facial paralysis who would like a procedure to provide some degree of movement to the weakened face is a muscle transplant to the face. As previously mentioned, this method involves at least one 6-12 hour surgery followed by days and weeks of intensive postoperative care. In the more commonly performed two-stage procedure, the sural nerve is harvested from the leg using a long, 5-10cm incision in the leg. The functional (non-paralyzed) side of the face is then opened widely, again using a large and visible facial incision from above the level of the ear down to the neck, and the branch of the facial nerve that stimulates a smile on the functional side is found. This nerve is then cut, and the sural nerve is the sutured to this nerve. The other end of the sural nerve graft is then tunneled beneath the skin in the upper lip to reach the contralateral (paralyzed) side of the face. This completes the first stage of the procedure, which can take 6-12 hours followed by an inpatient hospital stay of several days. Over a period of 6 to 12 months, if successful, the axons from the facial nerve of the functional side of the face will have grown into the nerve graft. Then, in the second stage of the procedure, the gracilis muscle, along with its primary feeding artery, vein and nerve, is carefully harvested from the inner thigh. This bulky muscle is the brought to the paralyzed side of the face, which again is widely opened using a large and visible facial incision. The end of the sural nerve is found in the upper lip and is sutured to the end of the nerve innervating the gracilis muscle. The artery and vein of the muscle will then need to be connected using special sutures to a prominent artery and vein in the face to provide the muscle with a viable blood supply; oftentimes, surgeons will need to enlarge the facial incision and explore the neck to find suitable vessels. Connecting two small blood vessels requires several hours of work under an operating microscope. The muscle itself is then sutured to the orbicularis oris muscle, which participates in the smile motion. Subsequently, the patient is monitored in the intensive care unit (ICU) for two to four days, and special equipment is used on an hourly basis to monitor the flow of the blood through the connected vessels; failure (clotting) of one or both of the vessels would require a return to the operating room and revision of the connections under general anesthesia. Drains to remove fluid and blood from the surgical sites (face and thigh) remain for days and require emptying and care by trained staff several times per day. Often times, the drain for the surgical site in the thigh remains for days to weeks, and if the patient is discharged from the hospital before the drain is ready to be removed, a visiting nurse will need to travel to the patient's home on a daily basis to help care for the drain. Again, results, if successful, do not emerge for another 6 to 12 months and would manifest as an upward movement of the corner of the mouth of, on average, 8 millimeters. In comparison, for example, in one embodiment, the present invention provides an implant system that only requires a short, two-hour outpatient surgery with a small 2-inch incision behind the ear and thus is completely hidden. Intraoperative testing can be conducted to ensure that all facial regions can be adequately stimulated by the placement of the intraneural electrode array. After 2-4 weeks of healing, the device can be tested and programmed and would be ready to be activated at that time. Optimally and with an "epidermal electronic" system to independently detect the motions of the functional side of the face, the patient would have full or nearly full and spontaneous function of the entire face, with contraction of paralyzed muscles proportional to that of the contralateral side.

(2) More efficient and faster. As described herein, in one embodiment, a patient using the present invention could receive immediate results within 2 to 4 weeks, depending on the comfort level of the surgeon to allow for implant activation in the setting of a healing surgical area. There is only one surgical site, compared to as many as four in the gracilis free flap option (leg, thigh, functional side of face, and paralyzed side of face). The surgery itself should take at most 2 hours, potentially can be done without general anesthesia (i.e. under local anesthesia with mild sedation), and can be done by any local general otolaryngologist in an outpatient surgery center. In contrast, and in the United States, as an example, the gracilis free flap surgery is only routinely performed in two facial nerve centers: the Massachusetts Eye and Ear Infirmary and Johns Hopkins Hospital.

(3) Less energy consuming. In accordance with various embodiments herein, a patient using this implant system does not need to spend a single night in the hospital, needs no surgical drains, and requires minimal post-operative care.

(4) Safer and less side effects. A patient undergoing the two-stage gracilis free flap procedures will require at least two surgeries, each lasting 6 to 12 hours under general anesthesia. General anesthesia alone is risky, and longer surgeries are strongly associated with more post-operative complications, including heart, lung and urinary tract problems, and stroke. The four surgical sites are furthermore each susceptible to complications, including bleeding, pain, infection, hematoma, and damage to important structures. Lengthy hospital stays are similarly associated with increased rates of serious and sometime fatal post-operative complications, including surgical site infections, pneumonia, sepsis, deep vein thrombosis, and pulmonary embolism. In contrast, in accordance with various embodiments described herein, a patient using our implant system would have only one small surgical site, undergo a technically-simple procedure with minimal risks, and not spend one day in the hospital.

Example 4

Currently Available Methods

Figure 2:
FIG. 2 depicts a strip of dense fascial connective tissue harvested from the thigh can be used to pull the corner of the mouth on the side of the paralysis upward to optimize oral competency and minimize drooling.

FIGS. 1 and 2 illustrate the currently available methods for treatment of facial paralysis. FIG. 1 depicts that the gracilis muscle, along with its principle nerve, artery and vein, was harvested from the thigh through a lengthy incision in the groin area. The muscle was then transplanted into the face in a 6-12 hour delicate surgery requiring an operating microscope, special equipment, and highly-specialized surgeons at one of very few facial nerve centers in the world. As one would expect, placement of a large thigh muscle into the thin tissues of the face creates substantial, asymmetric and unsightly bulk in the face.

FIG. 2 depicts a strip of dense facial connective tissue harvested from the thigh. This tissue could be used to pull the corner of the mouth on the side of the paralysis upward to optimize oral competency and minimize drooling.

Example 5

Device for Treating Facial Paralysis

Figure 4:
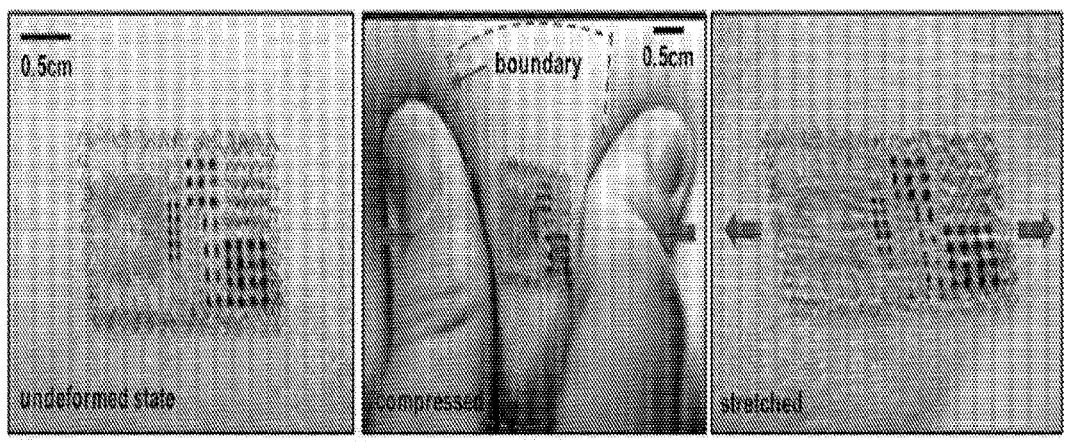
FIG. 4 depicts, in accordance with embodiments herein, a device that may include a sensor and transmitter and may be adapted to treat facial paralysis.

FIGS. 3 and 4 depict, in accordance with embodiments herein, a device for treating facial paralysis.

On the left, a conventional cochlear implant (CI) with a flexible electrode array which is inserted into the fluid-filled cochlea. In the CI system, the implant device receives signals from a microphone-transmitter worn on the ear and side of the head of the patient. Based on the frequencies of the sound information received, the implant discharges the appropriate amount of current into one or more of the 16-24 electrodes situated in the cochlea.

On the right, in one embodiment, the invention provides a device with a firm shank with multiple electrode sites that may be implanted into one or more facial nerves. Each of the electrodes would stimulate a set of neural fibers within the facial nerve responsible for specific movements of the face. Instead of receiving sound information, the device receives electromyogenic information from the opposite (normal and functional) side of the face and stimulates the corresponding musculature to achieve spontaneous and dynamic facial symmetry.

FIG. 4 depicts, in one embodiment, the use of the device to treat facial paralysis. In one example, one or more epidermal electronic devices were adhered to skin. In one embodiment, the epidermal electronic device has the ability to detect muscle, brain and heart activity, and wirelessly transmit the information to a recording display. In another embodiment, the epidermal electronic device was adapted to detect the contractions and extent of contractions of individual muscles of the functional side of the face and communicate this information to the implanted device on the paralyzed side of the face. In one embodiment, the implanted device on the paralyzed side of the face stimulated the corresponding muscles to achieve spontaneous and dynamic facial symmetry.

Example 6

Facial Paralysis and Treatment

Figure 5:
FIG. 5 depicts, in accordance with embodiments herein, examples of facial paralysis and effects of possible treatment.

FIG. 5 depicts, in accordance with embodiments herein, examples of facial paralysis and effects of treatment. (A) A young woman with right-sided permanent facial paralysis from a severe case of Bell's palsy that did not recover. Here she was attempting to smile but could only elicit movement on the left (functional) side of her face. Without any interventions, the muscles on the right side of her face would atrophy and scar down over a period of 2-3 years due to the inadequacy of neuro-stimulation from her damaged facial nerve. (B) In one embodiment, the invention provides a device implanted behind her right ear. The device comprises a penetrating multi-channel electrode array that was inserted into the mastoid segment of her right facial nerve in a technically-simple, two-hour surgery with a small incision immediately behind the auricle. Following surgery, technicians (audiologists) determine which muscles and actions were stimulated by each of the electrode contacts. (C) On her left (functional) side, an epidermal electronic device as described in FIG. 4 would be placed onto the skin and camouflaged by creating skin-colored sensors or with make-up. Alternatively, such technology could be implanted directly into the musculature. (D) In real-time, detected contractions of each left-sided facial muscle would trigger the epidermal electronic device to wireless communicate with the implant, which would then provide a programmed and graded stimulus to the appropriate electrode and generate a symmetric contraction of the corresponding muscle on the right (paralyzed) side. (E) This implant system would thus achieve dynamic and spontaneous facial symmetry.

Example 7

Additional Examples

Figure 6:
FIG. 6 depicts, in accordance with embodiments herein, the right side of the face of an anesthetized guinea pig is opened, and the facial nerve is identified.

The inventors placed an intraneural, penetrating, multi-channel electrode array (purchased from NeuroNexus) into the facial nerve of Guinea pigs and elicited isolated, independent movements of the auricle, face, and vibrissal pad (FIG. 6). Electromyographic signals from the functional side of the animal face were used to trigger corresponding movement in the contralateral side of the face. The facial nerve damage and paralysis model in animals were stimulated to better emulate the human condition. In one embodiment, the present invention provides a novel implant with a penetrating electrode array to be inserted into the cochlear nerve, rather than the fluid-filled cochlea. In FIG. 6, the lower branch of the facial nerve was penetrated by the electrode array, and isolated movements of the lower face and vibrissal pad could be triggered with individual electrodes on the array.

Example 8

Electrode Array and Stimuli

FIG. 7 illustrates a commercially available multichannel intraneural stimulating electrode array. The multi-channel intraneural stimulating electrode array had 16 iridium-plated sites, 703-$\mu m^2$ in area, arrayed at 100-$\mu m$ intervals spanning a distance of 1.5 mm along a single, 15-$\mu m$-thick silicon-substrate shank (FIG. 7). System 3 equipment from Tucker-Davis Technologies and custom software running in MAT-LAB were used for stimulus presentation. Electrical stimulus pulses were generated by a 16-channel current source controlled by a 16-channel digital-to-analog converter (TDT RX8). Stimuli were single charge-balanced biphasic electrical pulses, initially cathodic, 41 or 82 $\mu s$ per phase. The illustrated responses were obtained with stimulus charge levels of 26 to 41 nC per phase.

Figure 7A:
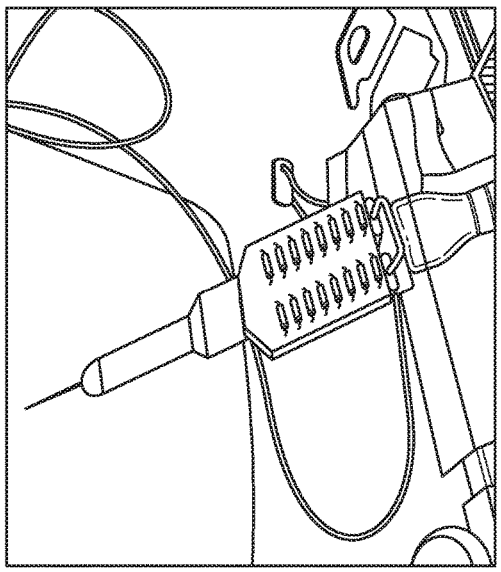
FIG. 7 depicts, in accordance with embodiments herein, a commercially available NeuroNexus multi-channel intraneural stimulating electrode array.
Figure 7B:
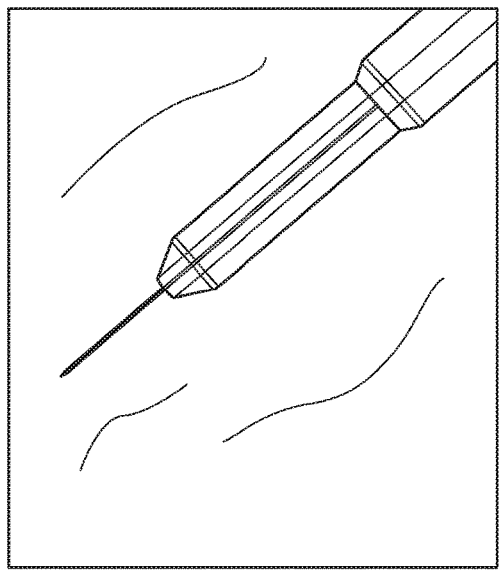
Figure 7C:
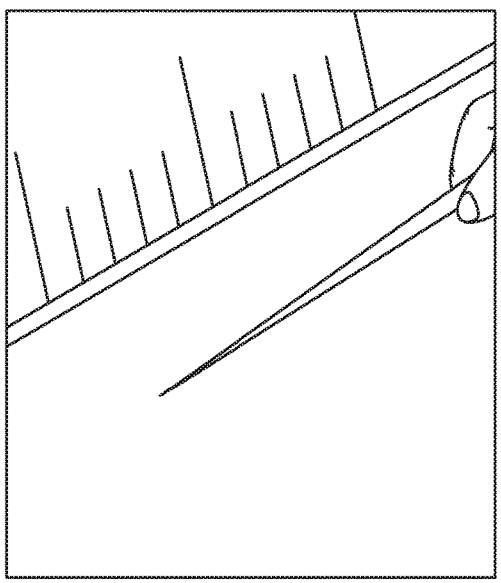
Figure 7D:
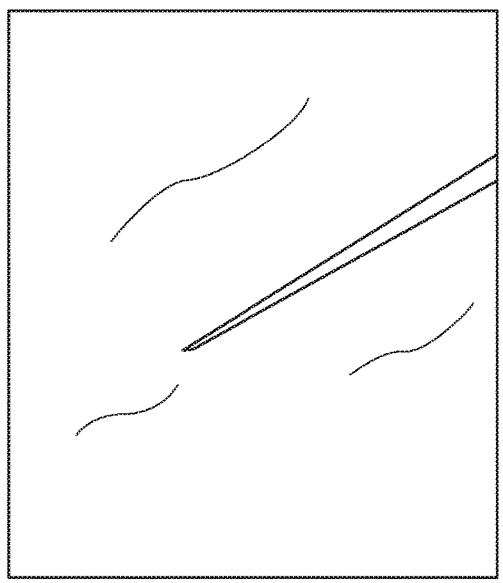

FIG. 7(A) illustrates a photograph of a NeuroNexus 16-channel stimulating electrode array in position on a micropositioner. FIG. 7(B) illustrates a microscopic picture of the shank and distal board. FIG. 7(C) illustrates a silicon-substrate shank with a metric ruler size reference. FIG. 7(D) illustrates a high-magnification microscopic photograph of the distal end of the penetrating shank; the 16 electrode sites can be seen. Superficial or proximal electrodes are those furthest from the tip of the array (to the right in this picture), while deep or distal electrodes are those closest to the array tip (to the left).

Example 9

Surgery

All the procedures described herein were performed with the approval of the University of California, at the Irvine Institutional Animal Care and Use Committee, according to the National Institutes of Health guidelines. The acute, terminal experiments were conducted in three barbiturate-anesthetized cats. Small incisions were made over four facial muscles, including the orbicularis oris, orbicularis oculi, nasalis, and levator auris longus, and each muscle was exposed. Needle electromyographic (EMG) electrodes were inserted into each muscle. An infra-auricular incision was made, and the trunk of the extra-temporal facial nerve was identified as it exits the temporal bone by the external auditory canal. The dense epineurium was penetrated with a 30 gauge needle, and the array was introduced into the facial nerve proximal to the bifurcation into the dorsal and ventral rami with the aid of a micro-positioner and with the goal of inserting all 16 stimulating sites in neural tissue. The site and angle of insertion were not programmed or pre-determined; positioning of the array was dictated by the surgical anatomy and access to the nerve with the micro-positioner. The electrode array was advanced until resistance was detected. Each of the intra-neural sites were stimulated, one at a time, and EMG voltage responses from the four selected facial muscles were recorded by the nerve integrity monitoring system (NIM Response 2.0, Medtronic Inc.). To vary the neural populations stimulated, the stimulating electrode array was removed and replaced into the nerve in varying trajectories and angles along the course of the exposed facial nerve trunk, and each electrode site was again stimulated.

Stimulation through individual electrodes activated nerve populations selectively, often resulting in EMG activity in individual muscles. Selective activation of two or more distinct muscles was successfully achieved via a single placement of the multi-channel electrode array by selection of appropriate stimulation channels.

Figure 8:
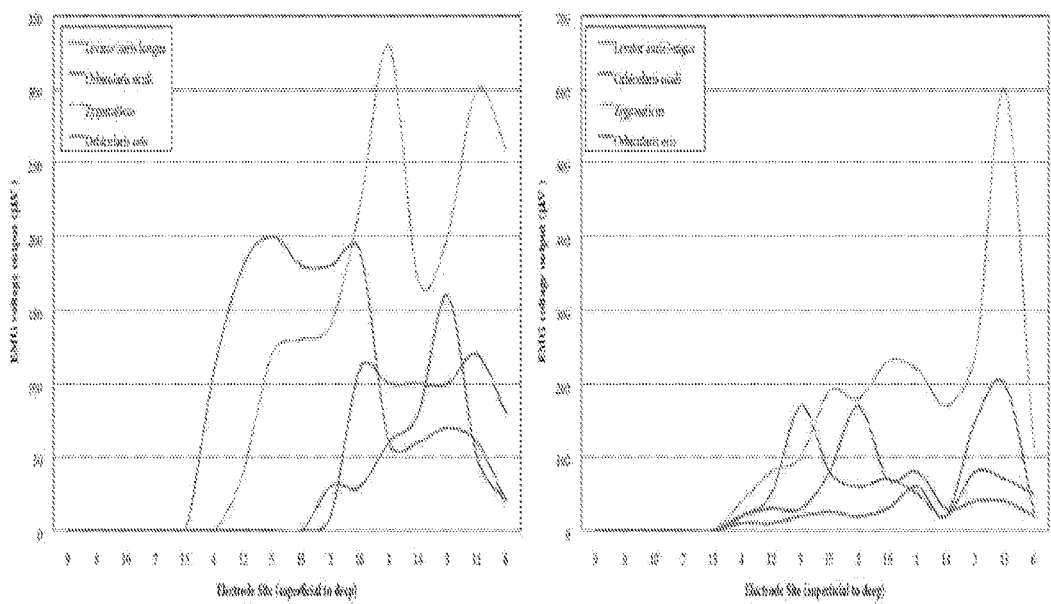
FIG. 8 depicts, in accordance with embodiments herein, a graphic representation of successive stimulation of channels from superficial (electrode #9) to deep (electrode #6) electrodes, from left to right on the x-axis, and the corresponding EMG voltage response of distinct muscles on the y-axis.

FIG. 8 depicts, in accordance with embodiments herein, a graphic representation of successive stimulation of channels from superficial (electrode #9) to deep (electrode #6) electrodes, from left to right on the x-axis, and the corresponding EMG voltage response of distinct muscles on the y-axis. Stimulation through the most superficial channels failed to elicit any substantial neural activity, likely due to the channels being out of the nerve. On the left [cat 2, position 1], the middle channels robustly stimulated the levator auris longus muscle, while the deeper channels activated the orbicularis oculi, zygomaticus, and orbicularis oris (current level: 35 dB re 1 $\mu Amp$; phase duration: 41 $\mu s$; pulse duration: 200 $\mu s$). At a different insertion site on the right [cat 2, position 3], a unique pattern of stimulation was recorded (current level: 45 dB re 1 $\mu Amp$; phase duration: 41 $\mu s$; pulse duration: 200 $\mu s$). FIG. 8 [cat 2, position 1] shows representative data of EMG voltages from individual channel stimulation of the main trunk of the facial nerve. Stimulation through the most proximal/superficial channels failed to elicit any substantial neural activity, which was the consequence of the superficial electrodes being out of the nerve. The middle channels of the array most robustly stimulated the levator auris longus muscle, while the deepest channels activated the remaining three muscles to varying, stronger degrees. A similarly diverse pattern of maximal and minimal stimulation responses was found in a subsequent insertion of the array into the facial nerve in a different location and angle (FIG. 8 [cat 2, position 3]). In one embodiment, the inventors have shown movement of the auricle, lateral face, and upper lip, with insertions of the array into the nerve.

Figure 9:
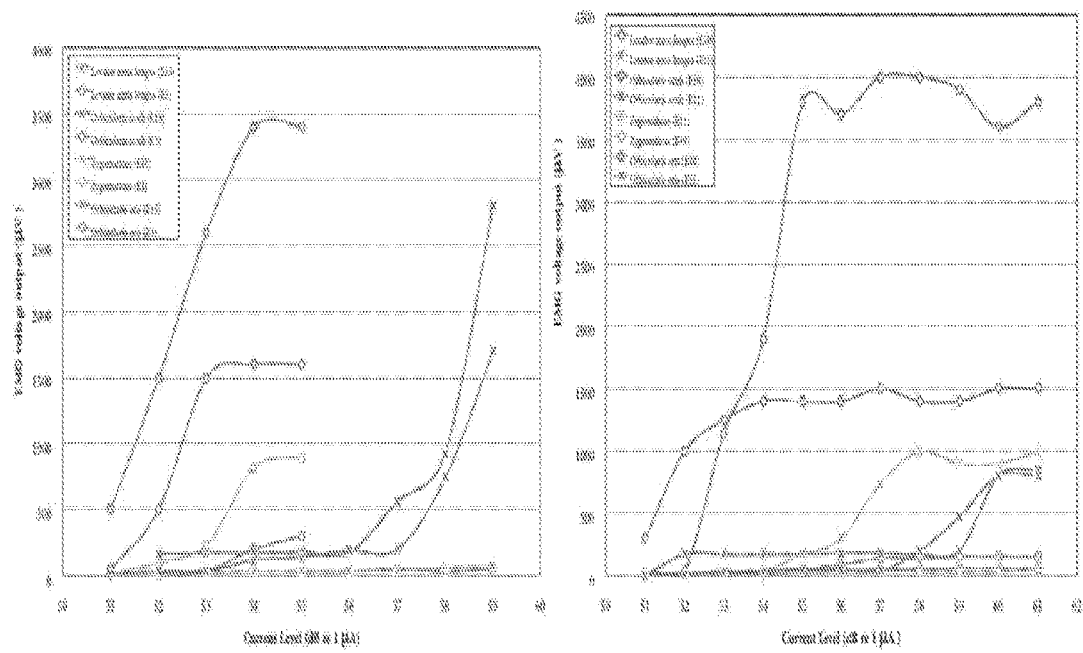
FIG. 9 depicts, in accordance with embodiments herein, a graphic representation of escalating stimulation current levels of a single electrode on the x-axis, with correspondingly increasing EMG voltage responses on the y-axis.

FIG. 9 illustrates, in accordance with embodiments herein, a graphic representation of escalating stimulation current levels of a single electrode on the x-axis, with correspondingly increasing EMG voltage responses on the y-axis. Also demonstrated is the distinct voltage responses of different muscles to graded stimulation of a superficial electrode (electrode #15) compared to a distant, deeper electrode (electrode #3) [cat 3, position 1]. At high levels of muscular contraction, gross movement of the head of the cat will endanger the fragile stimulating array residing in the facial trunk, and accordingly electrode #3 could only be stimulated up to 55 dB re 1 µAmp. On the right is a similar plot from stimulation of electrode #10 and electrode #11 at a different array insertion site [cat 3, position 2]. As illustrated in FIG. 9 (cat 3, position 1 & 2), increasing stimulation current levels resulted in increasing EMG voltage responses. Furthermore, in one embodiment, the inventors found that graded stimulation of one electrode (electrode #3, #10, respectively) elicited voltage responses of different muscles to different extents when compared to those from stimulation of a distant electrode (electrode #15, #11, respectively). In one embodiment, the inventors demonstrated fine contractions of the face with delivery of short but high levels of current that activates several facial muscles.

Figure 10:
FIG. 10 depicts, in accordance with embodiments herein, video still images of relaxed left facial muscles (A), prior to sustained facial contraction with three-second-long, high level current pulses delivered to a single electrode on the intraneural array (B).

In another embodiment, the inventors have demonstrated sustained facial contraction with three-second-long, high level current delivery to the nerve. FIG. 10 illustrates video still images of relaxed left facial muscles (A), prior to sustained facial contraction with three-second-long, high level current pulses delivered to a single electrode on the intraneural array (B).

Example 10

Selective Stimulation of Facial Muscles with a Penetrating Intraneural Multichannel Electrode Array in a Feline Model In one example, the inventors performed experiments in animals with normal facial function to study facial nerve rehabilitation. These examples included experiments on three cats (*felis catus*). Four facial muscles (orbicularis oris, orbicularis oculi, nasalis, intermedius scutulorum) were monitored with a standard electromyographic (EMG) facial nerve monitoring system with needle electrodes. The main trunk of the facial nerve was exposed and a 16 channel penetrating electrode array was placed into the nerve. Electrical current pulses were delivered to each stimulating electrode individually. Elicited EMG voltage outputs were recorded for each muscle.

In one embodiment, the inventors observed that stimulation through individual channels selectively activated restricted nerve populations, resulting in selective contraction of individual muscles. Increasing stimulation current levels resulted in increasing EMG voltage responses. In one embodiment, selective activation of two or more distinct muscles was successfully achieved via a single placement of the multichannel electrode array by selection of appropriate stimulation channels.

In some embodiments, the electrode material and the surface area of the electrode may be changed to improve the selectivity of stimulation. In another embodiment, continuous use of the method described herein over a period of months or years may provide the face with muscular tone. In another embodiment, the contralateral good side may be detected to drive stimulation.

In sum, in one embodiment, the inventors have shown that a penetrating electrode array was able to selectively stimulate restricted fiber populations within the facial nerve and to selectively elicit contractions in specific muscles and regions of the face. In another embodiment, a facial nerve implant system may be developed using this process. In one embodiment, this approach elucidated a new approach for restoring facial motion in patients with facial nerve paralysis.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating facial paralysis, comprising:
   implanting an array of electrodes in or near a paralyzed side of a face, wherein the array is connected to a receiver stimulator; and
   using at least one sensor configured to detect both a presence and an extent of contractions of at least one healthy muscle in the non-paralyzed side of the face;
   wherein the at least one sensor is further configured to send contraction signals to the receiver stimulator;
   based on the detection of contractions of the at least one healthy muscle, mapping muscle movements of the at least one healthy muscle;
   based on the mapping, transmitting, from the receiver stimulator, a stimulation to an anatomically corresponding unhealthy muscle or unhealthy nerve on the paralyzed side of the face;
   whereby symmetric contraction occurs between the corresponding unhealthy muscle and the at least one healthy muscle.

2. The method of claim 1, wherein the array of electrodes are positioned in one or more firm shanks.

3. The method of claim 1, wherein the stimulation of the unhealthy nerve comprises independently exciting specific nerve fiber populations that generate isolated movements in the said nerve fiber populations.

4. The method of claim 1, wherein the receiver stimulator is configured to receive electromyogenic information from the non-paralyzed side of the face.

5. The method of claim 1, wherein the stimulation is graded to provide an escalating current level.

6. The method of claim 1, wherein the symmetric contractions occur simultaneously.

7. A method of treating facial paralysis, comprising:
- placing a device on or near at least one of an unhealthy nerve and an unhealthy muscle, both of which are associated with a paralyzed side of a face;
- wherein the device includes an array of electrodes and a receiver stimulator;
- wherein the receiver stimulator is configured to receive electromyogenic information from at least one of the unhealthy nerve and the unhealthy muscle;
- using at least one sensor configured to:
  - to detect contractions of at least one healthy muscle in the non-paralyzed side of the face, wherein the at least one healthy muscle anatomically corresponds to the at least one unhealthy muscle; and
  - send contraction signals to the receiver stimulator based on the detection of contractions of the at least one healthy muscle;
- transmitting, from the receiver stimulator, a graded stimulation to the at least one of the unhealthy nerve and the unhealthy muscle;
- wherein the graded stimulation is an escalating current level that generates contraction of the unhealthy muscle simultaneously with contraction of the healthy muscle.

8. The method of claim 7, wherein the device further includes a grounding electrode.

9. The method of claim 7, wherein the sensor is an epidermal or intramuscular electronic device.

10. The method of claim 7, wherein the sensor detects both a presence and an extent of contractions.

11. The method of claim 7, wherein the receiver stimulator wirelessly receives the electromyogenic information.

\* \* \* \* \*